United States Patent
Hussein et al.

(12) 
(10) Patent No.: US 6,258,119 B1
(45) Date of Patent: Jul. 10, 2001

(54) IMPLANT DEVICE FOR TRANS MYOCARDIAL REVASCULARIZATION

(75) Inventors: Hany Hussein, Costa Mesa; Stanislaw Sulek, Mission Viejo, both of CA (US)

(73) Assignee: Myocardial Stents, Inc., CA (US)

( * ) Notice: Subject to any disclaimer, the term of this patent is extended or adjusted under 35 U.S.C. 154(b) by 0 days.

(21) Appl. No.: 09/293,632

(22) Filed: Apr. 15, 1999

Related U.S. Application Data

(60) Continuation of application No. 09/008,695, filed on Jan. 19, 1998, now abandoned, which is a division of application No. 08/739,724, filed on Nov. 7, 1996, now Pat. No. 5,810,836.

(51) Int. Cl.$^7$ ........................................ A61F 2/06
(52) U.S. Cl. ...................... 623/1.22; 623/1.31; 623/1.36; 606/108
(58) Field of Search ................. 623/1.22, 1.31, 623/1.36; 606/108

(56) References Cited

U.S. PATENT DOCUMENTS 5,466,242 * 11/1995 Mori ...................................... 606/198
5,500,013 * 3/1996 Buscemi et al. ..................... 623/1.22

\* cited by examiner

*Primary Examiner*—Corrine McDermott
*Assistant Examiner*—Choon P. Koh
(74) *Attorney, Agent, or Firm*—James G. O'Neill

(57) ABSTRACT

A myocardial implant for insertion into a heart wall for trans myocardial revascularization (TMR) of the heart wall. The TMR implant provides for means to promote the formation of new blood vessels (angiogenesis), and has a flexible, elongated body that contains a cavity and openings through the flexible, elongated body from the cavity. The TMR implant includes a coaxial anchoring element integrally formed at one end for securing the TMR implant in the heart wall.

19 Claims, 15 Drawing Sheets

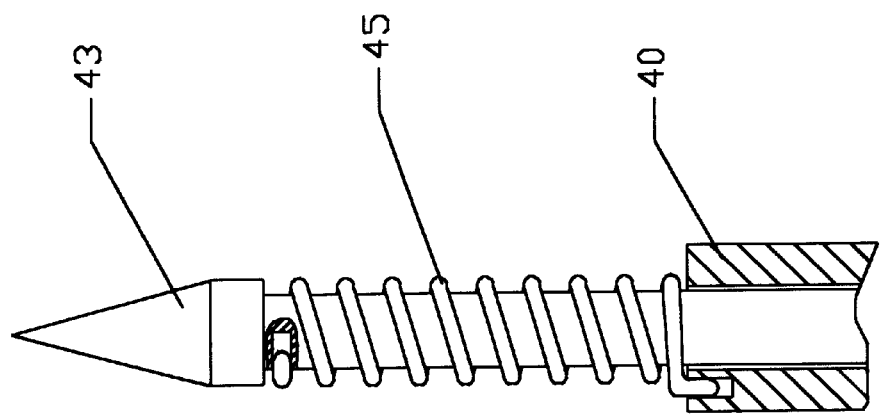
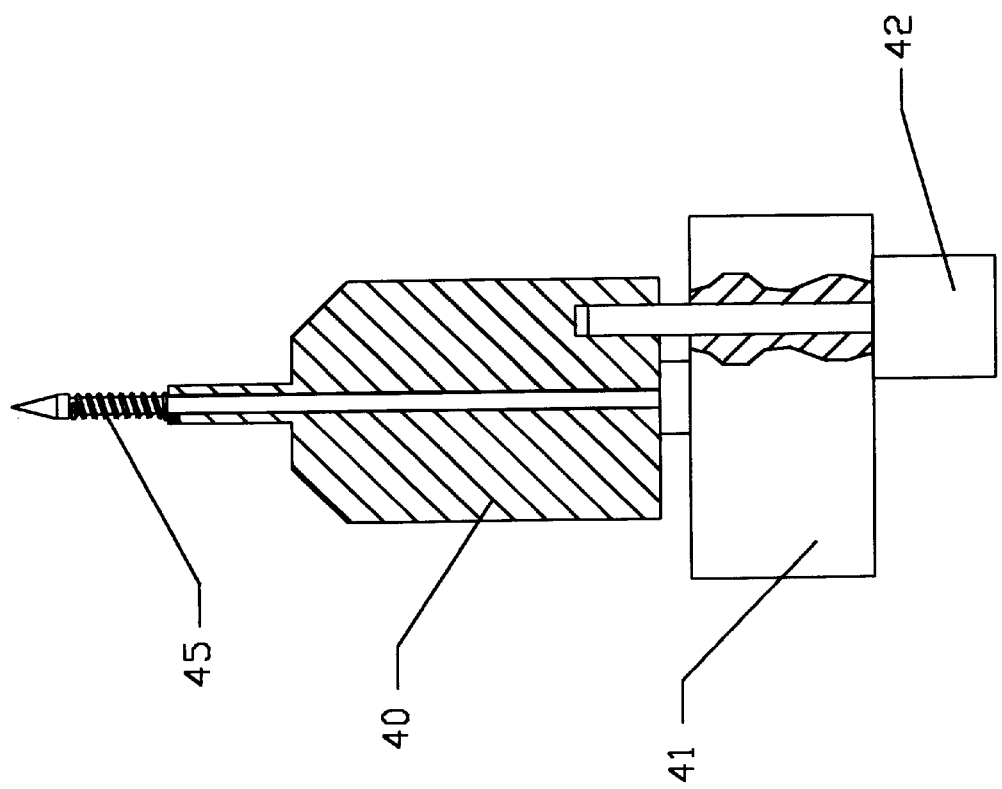
FIGURE 8D
FIGURE 8C

IMPLANT DEVICE FOR TRANS MYOCARDIAL REVASCULARIZATION

This is a continuation-in-part of pending application serial number 09/008,695, filed Jan. 19, 1998, now abandoned which was a divisional application of application Ser. No. 08/739,724, filed Nov. 7, 1996, now U.S. Pat. No. 5,810,836.

BACKGROUND OF THE INVENTION

1. Technical Field

This invention is generally directed to the fields of cardiac surgery and interventional cardiology, and particularly, to mechanical devices and methods suited for improving blood flow to a heart muscle by Trans Myocardial Revascularization (TMR).

2. Description of Related Art

Symptomatic occlusive coronary artery disease that does not respond to medical or interventional treatment is a major challenge for cardiac surgeons and cardiologists. The discovery of sinusoidal communications within the myocardium (Wearns, 1993) has motivated researchers to attempt various methods for myocardial revascularization based on the existence of this vascular mesh network. These methods aimed at the delivery of oxygenated blood to the vicinity of the sponge-like sinusoidal plexus in order to restore blood flow to the ischemic myocardium. Several investigators have attempted to deliver oxygenated blood directly from the left ventricle into the myocardial sinusoids by employing needle acupuncture to create transmural channels. Trans Myocardial Revascularization (TMR) has been employed clinically (Mirhoseini, 1991) by utilizing a CO2 laser for creating transmural channels in the left ventricular myocardium. These channels are typically 1 mm in diameter and extend throughout the wall thickness (15 to 20 mm) of the ventricle. It has been hypothesized that TMR works by providing a fluid conduit for oxygenated blood to flow from the endocardiac surface (heart chamber) to the mycardium inner layers thus providing oxygenated blood to myocardial cells without requiring coronary circulation; as in reptiles. Animal studies in the canine model have demonstrated the feasibility of this approach. In these studies, an increase in survival rate was demonstrated in dogs that had transmural channels and ligated coronary arteries.

While clinical studies have demonstrated improvements in patient status following TMR, histological studies indicate that the channels created for TMR tend to close shortly after the procedure. Randomized, prospective clinical trials are underway to examine the merit of TMR compared to medical treatment. In the meantime, research studies are being initiated to provide an understanding of the mechanism by which TMR actually works.

It would be desirable to develop means for maintaining the patency of TMR channels within the myocardium. Furthermore, it would be desirable to create channels for TMR without requiring the use of an expensive and bulky laser system, such as currently available CO2 laser systems. This invention provides the desired means for producing trans myocardial channels that are likely to remain patent, and that do not require laser application for generating these channels.

Specifically, the objective of the present invention is to generate needle-made channels or space in the ischemic heart wall, and to deliver or place in these channels (or space) an array of implants or stents in order to provide improved means for supplying blood nutrients to ischemic myocardial tissue. Nutrients flow to the stented channels from the ventricular cavity, and diffuse from the side ports of the stent to the myocardial tissue through the needle-made channels. Our disclosed TMR approach of producing stented, needle-made, channels is supported by the recent scientific evidence (Whittaker et al, 1996) that needle-made transmural channels can protect ischemic tissue. Whittaker et al. assessed myocardial response at two months to laser and needle-made channels in the rat model which has little native collateral circulation. They found that channels created by a needle can protect the heart against coronary artery occlusion, and that these channels provide greater protection to ischemic tissue than channels created by laser. The limitation of needle-made channels is early closure (Pifarre, 1969). The disclosed implant approach offers a possible solution to the early closure problem, while taking advantage of simple and effective needle-made channels for TMR.

SUMMARY OF THE INVENTION

This invention provides implant and needle means for creating and maintaining a patent lumen in the diseased myocardium. This implant provides a conduit for the flow of blood nutrients from the ventricular chamber to the intramyocardial vascular network. This implant can be used as the sole therapy or as an adjunctive therapy to other forms of TMR. Revascularization of the myocardium can be achieved and maintained by creating implanted, needle-made, channels within the myocardial tissue. These channels can allow blood nutrients within the left ventricular cavity to find direct access to ischemic zones within the ventricular wall independent of access through the coronary arteries.

Various configurations of implants are disclosed; including flexible and rigid implants, screw implants, sleeve implants, and others. Manual or powered devices are disclosed for the delivery or placement of implants into a heart wall. The proximal end of each implant terminates at the epicardial surface and provides mechanical holding means to prevent implant detachment and leakage of blood from the ventricle. Each implant is designed so as to maintain an adequate pressure gradient between the left ventricle and the myocardial tissue in order to maintain the flow from the ventricular cavity to the myocardial tissue of blood nutrients.

Furthermore, the disclosed TMR implants may define a cavity, which can be pressurized during operation so as to enhance the flow of blood to myocardial tissue. Each such implant can essentially operate as a mini-pump that is activated by myocardial contraction or by an external energy source.

Several embodiments of the implant and delivery systems therefor are proposed. The implants include the following: flexible spring, rigid sleeve, hollow screw, helical screw, and pumping (active) implants. The implants can be prestressed or made from memory metal in order to minimize the size of the implant during the insertion process. The various delivery systems are described below.

BRIEF DESCRIPTION OF THE DRAWINGS

FIGS. 8A–8I illustrate an alternate TMR implant and a delivery system for insertion of this TMR implant into a heart wall;

DESCRIPTION OF PREFERRED EMBODIMENTS

The following description is provided to enable any person skilled in the art to make and use the invention, and sets forth the best modes contemplated by the inventors of carrying out their invention. Various modifications, however, will remain readily apparent to those skilled in the art, since the generic principles of the present invention have been defined herein specifically to provide for improved implants and an improved delivery system for such elements.

Figure 1:
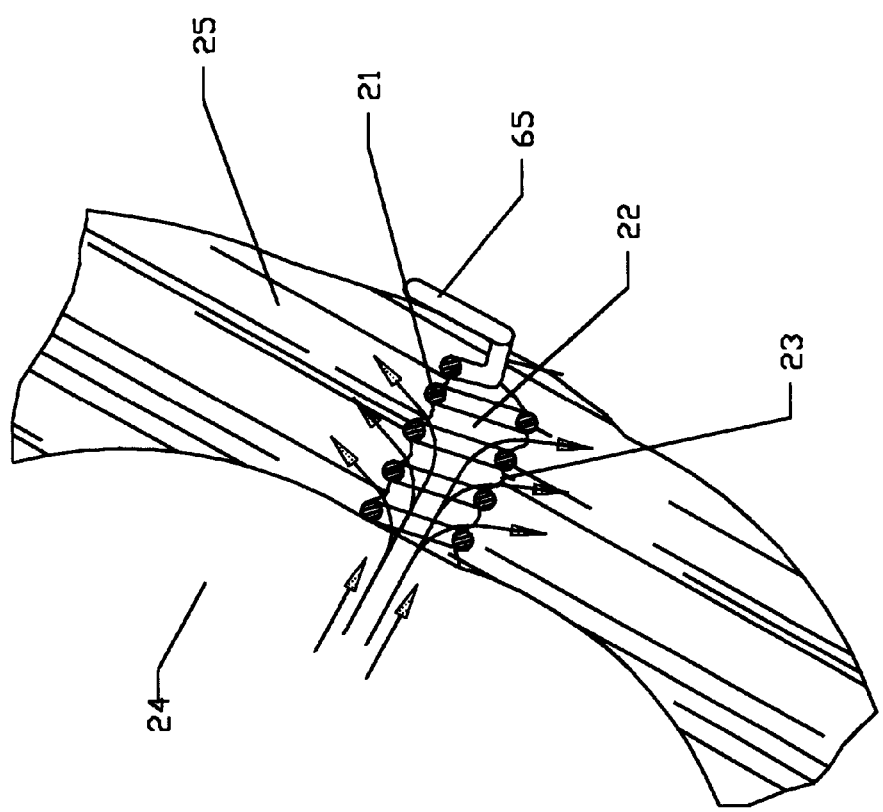
FIG. 1 is a cross-sectional view of a TMR implant inserted in a heart wall. The implant is configured as an expandable coil spring having an integral anchoring wire.

FIG. 1 shows a flexible TMR stent (hereinafter "myocardial implant", or "implant") having a coil spring body 21 defining a cavity 22 and spacing 23 between the turns of said spring body. In this embodiment, blood nutrients flow from the heart chamber 24 to the heart wall 25 by passage through the coil spring cavity 22 and spacing 23. An anchoring wire 65 secures the implant to the heart wall.

Figure 2:
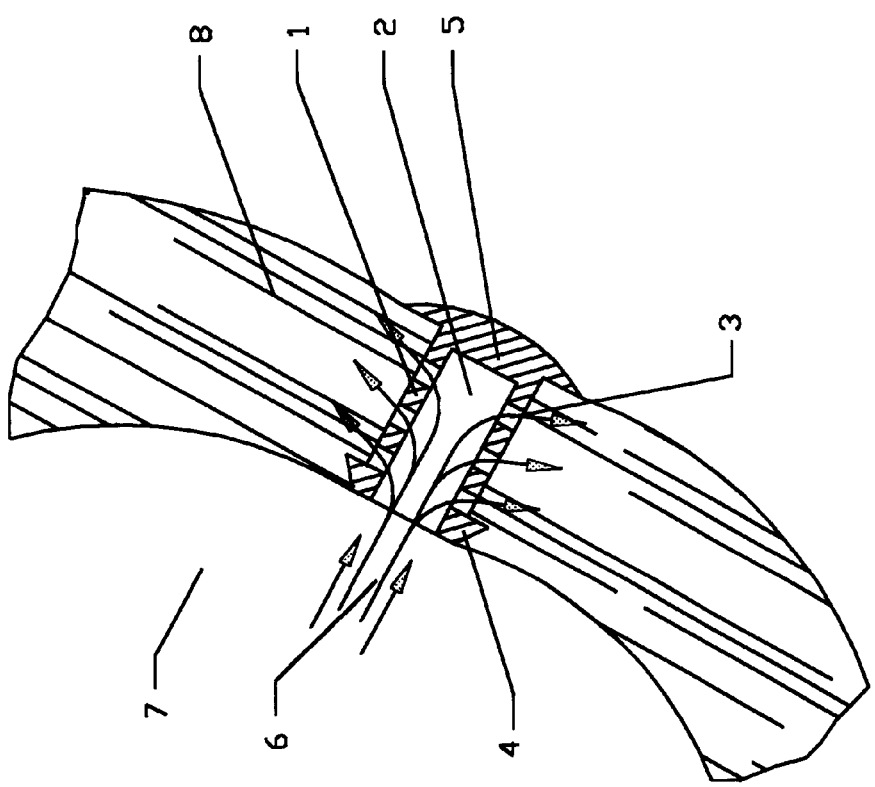
FIG. 2 is a cross-sectional view of a TMR implant having the configuration of a rigid sleeve having side ports.

FIG. 2 shows a myocardial implant that comprises a tubular body 1, cavity 2, side ports 3, retainer 4, and closure 5. In this embodiment, blood nutrients 6 are transported from the heart chamber (ventricle) 7, through the cavity 2 and side ports 3, to the heart wall 8.

Figure 3:
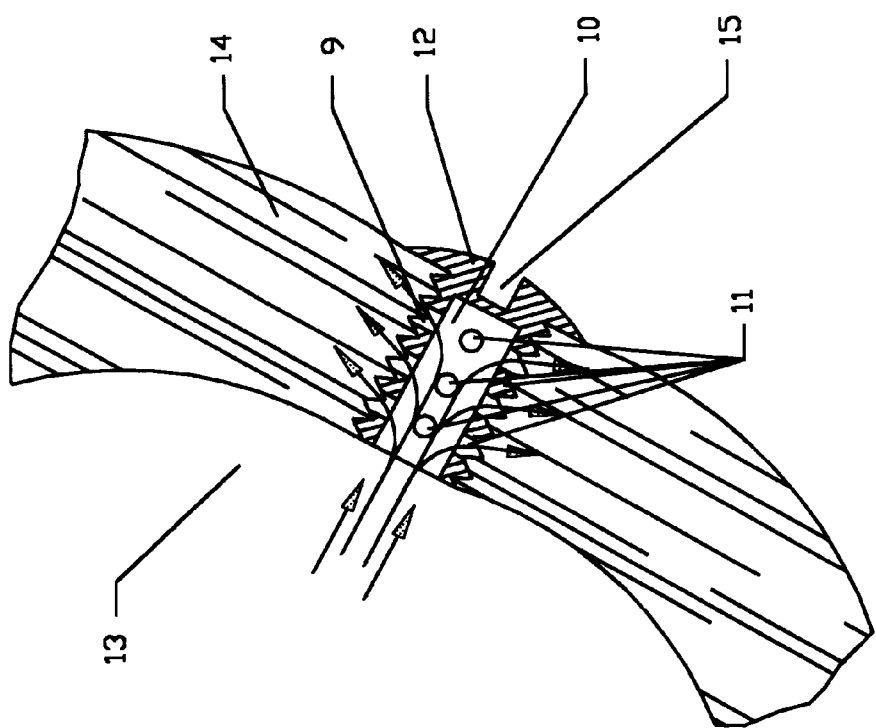
FIG. 3 is a cross-sectional view of a TMR implant having the configuration of a hollow screw with side ports.

FIG. 3 shows a myocardial implant that is configured as a hollow screw having a threaded body 9, cavity 10, side ports 11, closure 12, and slot 15. In this embodiment, blood nutrients flow from the heart chamber 13 to the heart wall 14 by passage through the cavity 10 and side ports 11.

Figure 4:
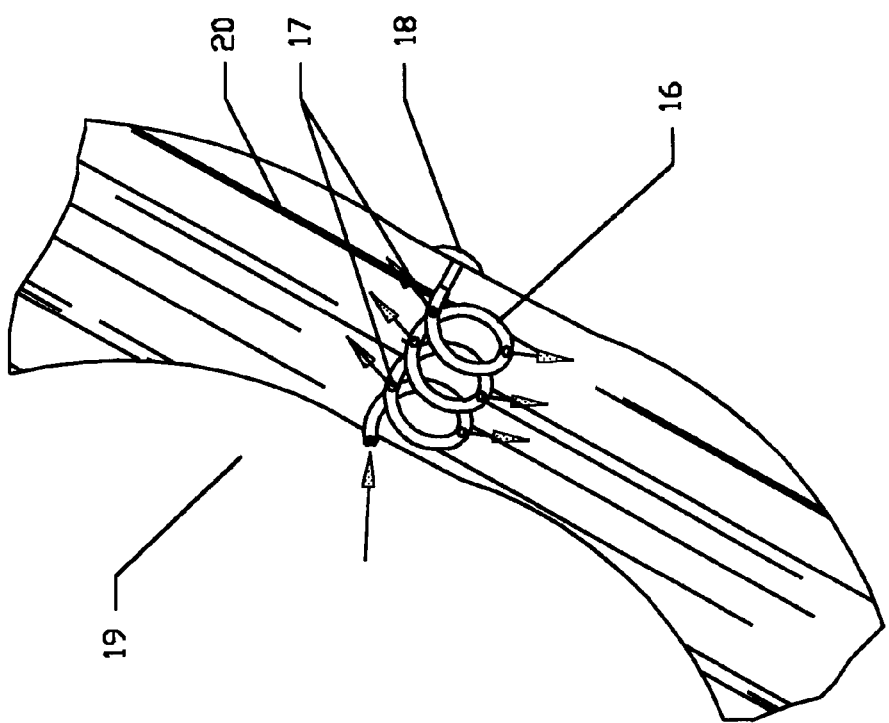
FIG. 4 is a cross-sectional view of a TMR implant having the configuration of a wire screw.

FIG. 4 shows a myocardial implant that is a hollow wire screw having an elongated hollow coil body 16, side ports 17, and anchor 18. In this embodiment, blood nutrients flow from the heart chamber 19 to the heart wall 20 by passage through the hollow core of the wire 16 and side ports 17.

Figure 5:
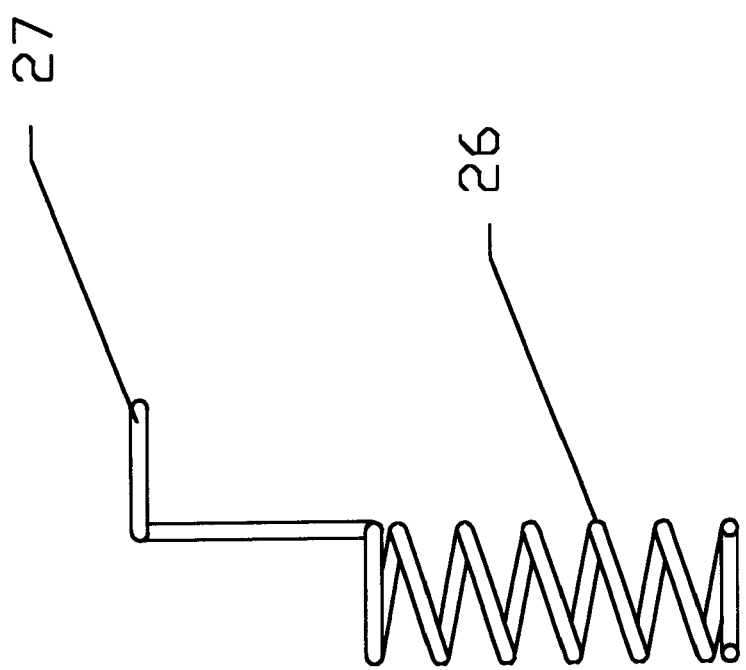
FIG. 5 is a cross sectional view of a flexible implant having an integral anchoring coil.

FIG. 5 shows a flexible myocardial implant having a coil body 26 and an anchoring coil 27 which is an integral part of the myocardial implant. The anchoring coil prevents detachment of the myocardial implant from the heart wall.

Figure 6:
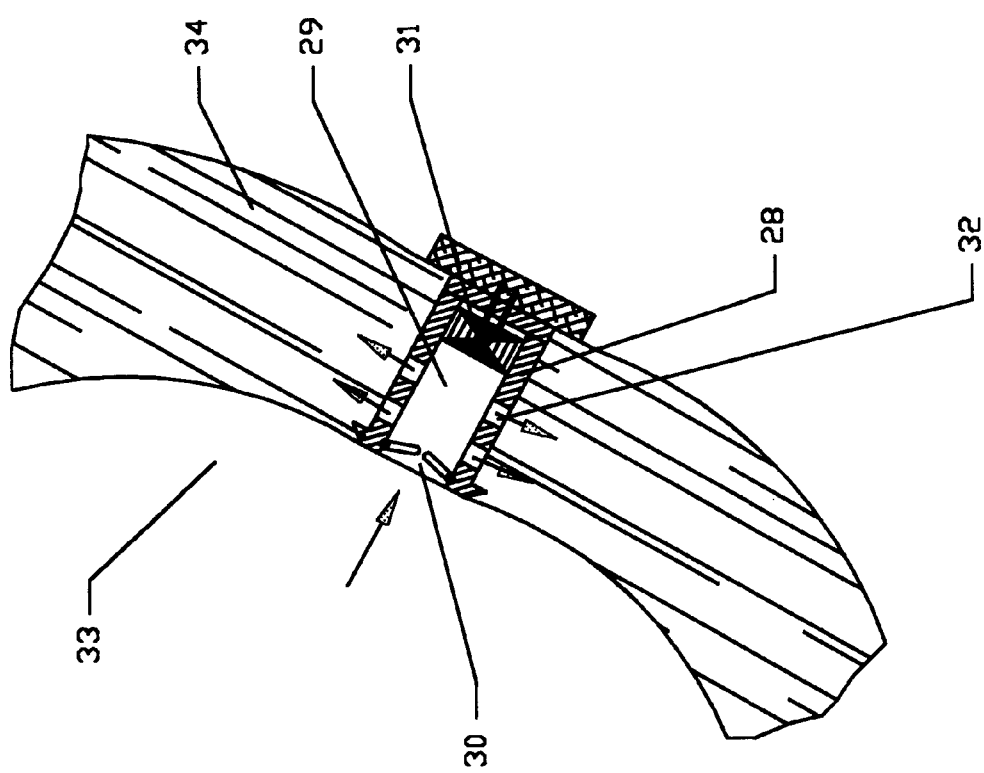
FIG. 6 is a cross-sectional view of a TMR implant having the configuration of a miniature pump.

FIG. 6 shows a myocardial implant having a cylindrical body 28 defining a cavity 29. A valve 30, pumping element 31, and side ports 32 are situated within the cavity 29. In this embodiment, blood nutrients flow from the heart chamber 33 to the pumping cavity 29. The valve 30 is activated and the pumping element 31 operates to displace the blood from the pumping cavity 29 through side ports 32 to the heart wall 34.

Figure 7:
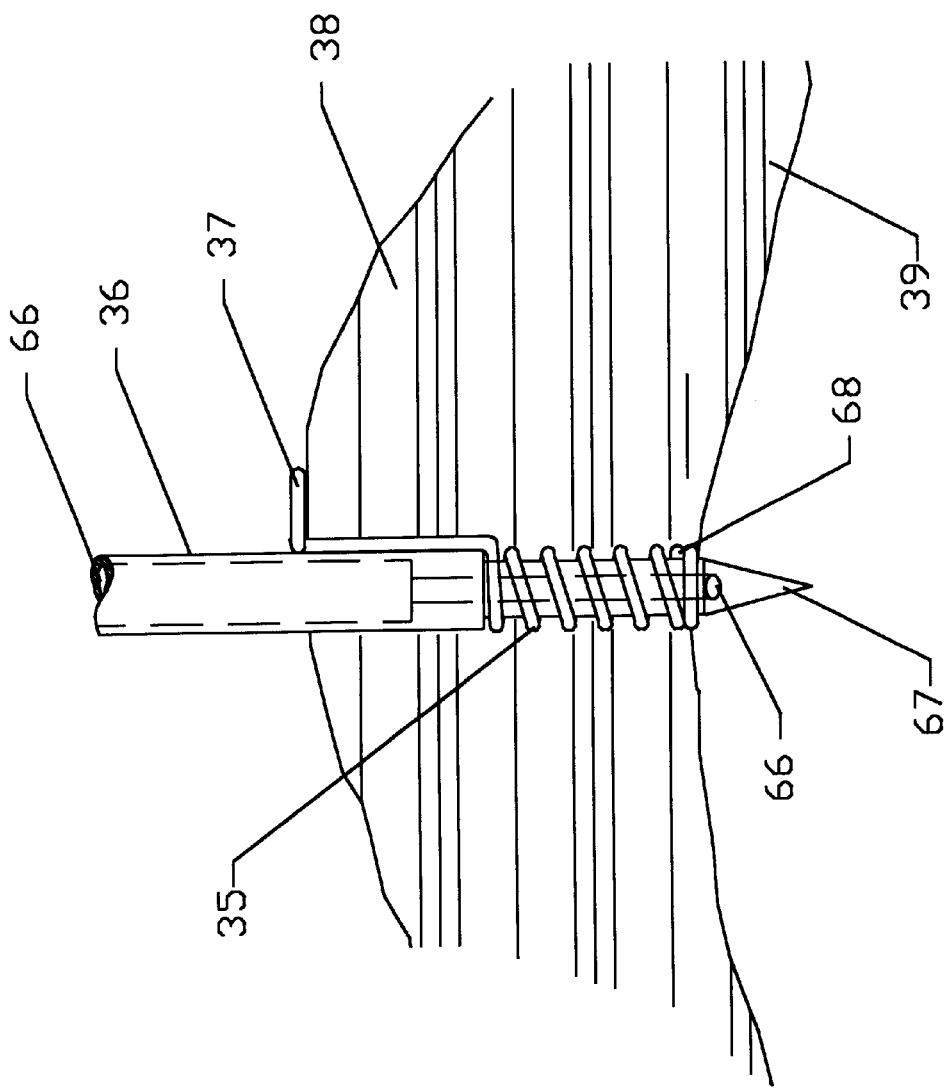
FIG. 7 shows a TMR delivery device and method for insertion of a TMR implant into a heart wall.
Figure 12:
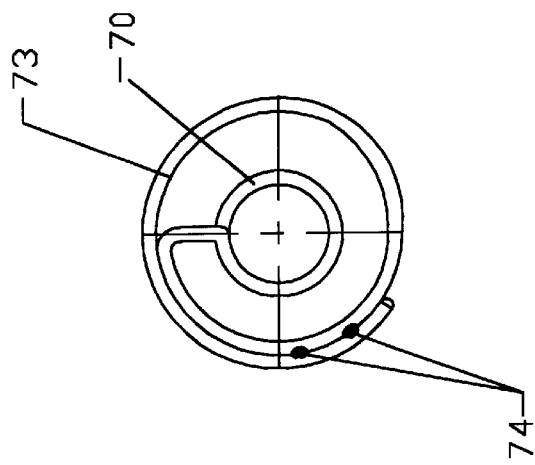
FIG. 12 is an end view of the implant of FIG. 11.
Figure 11:
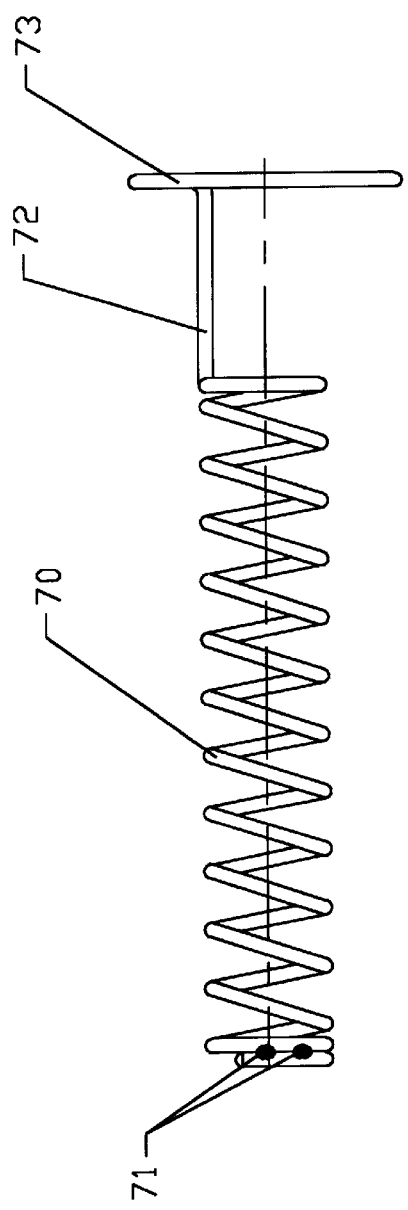
FIG. 11 is a front elevational view of an alternate implant (myocardial stent)

FIG. 7 shows the construction and method of use of one embodiment of a delivery device for creating a pathway in the heart wall and for placement of a myocardial implant in this pathway. In this first embodiment, a needle obturator 36 carries a myocardial implant 35 having an anchoring wire 37, which may be offset from the myocardial implant, as shown in FIG. 7, or aligned with the myocardial implant, as shown in FIGS. 11 and 12. The obturator and myocardial implant are inserted through the heart wall 38 until the endocardiac surface is reached. After the endocardiac surface 39 of the heart wall is reached, the obturator 36 is removed, as by turning or unscrewing the same, thereby leaving the myocardial implant 35 embedded in the heart wall. Additional improvements include a fluid channel 66 that is formed in the obturator body to provide an indication that the obturator's distal end 67 has crossed the endocardiac surface 39.

Figure 8B:
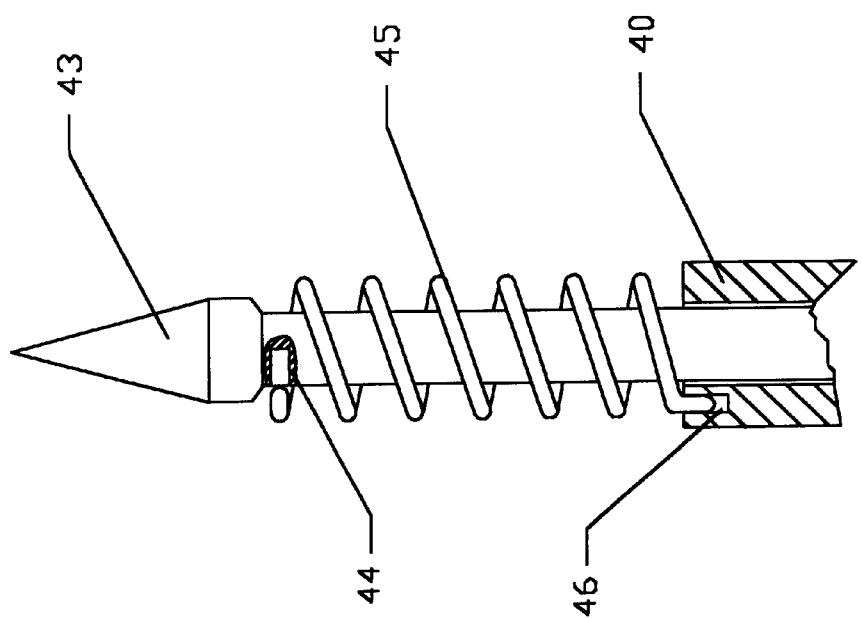
Figure 8A:
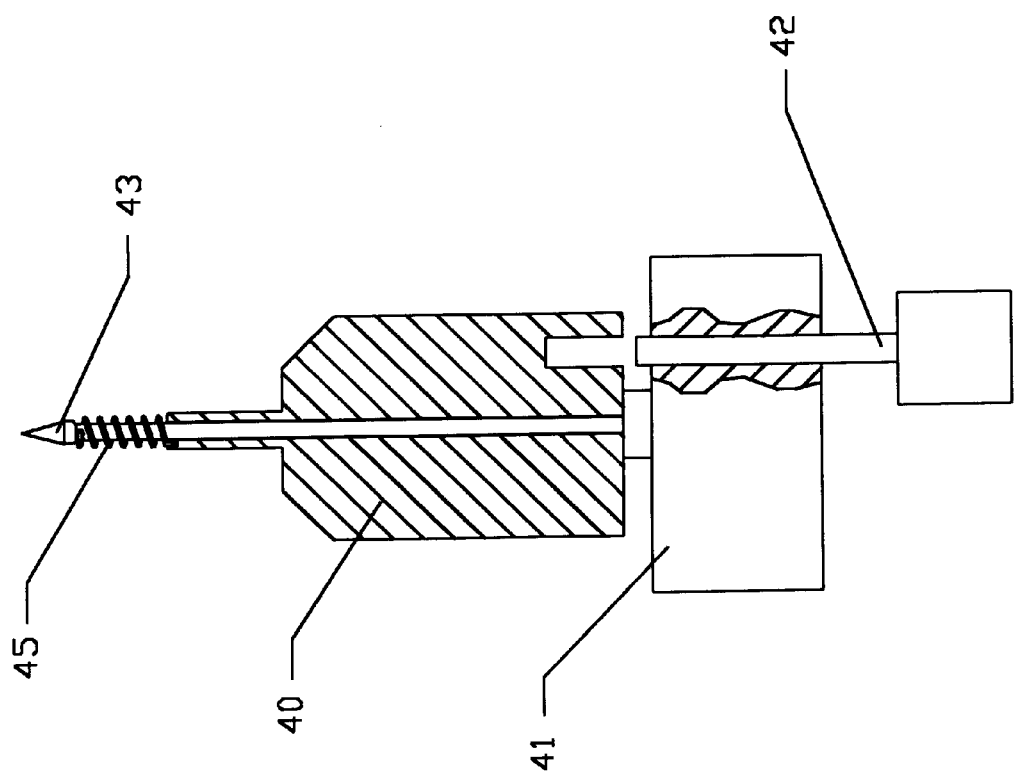

FIGS. 8A through 8I show the construction of an alternate myocardial implant and a second embodiment of a delivery system for placement of the alternate implant in a heart wall. FIG. 8A shows a delivery system having a pin 40 and handle 41 having a locking device 42. An obturator 43 is mounted in the pin 40. The obturator 43 has a recess 44 (FIG. 8B) to engage the distal end of a myocardial implant 45. The pin 40 has a recess 46 (FIG. 8B) to engage the proximal end of the implant 45.

Figure 8F:
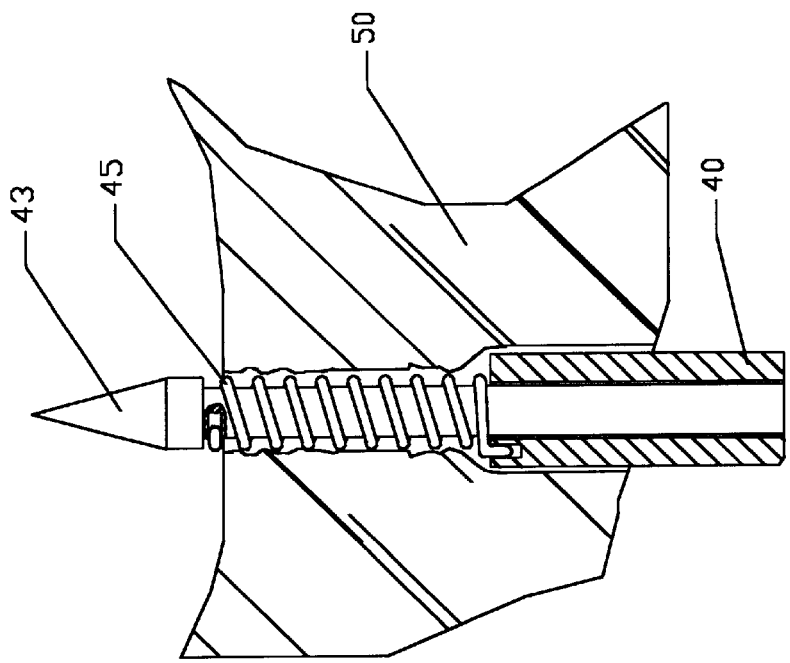
Figure 8E:
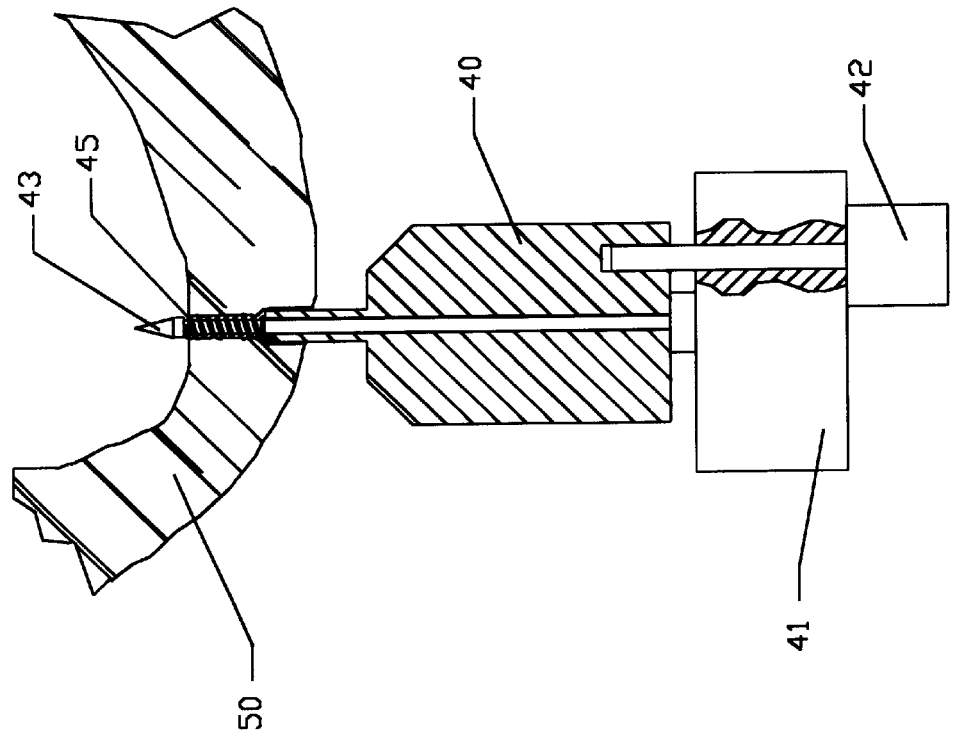
Figure 8I:
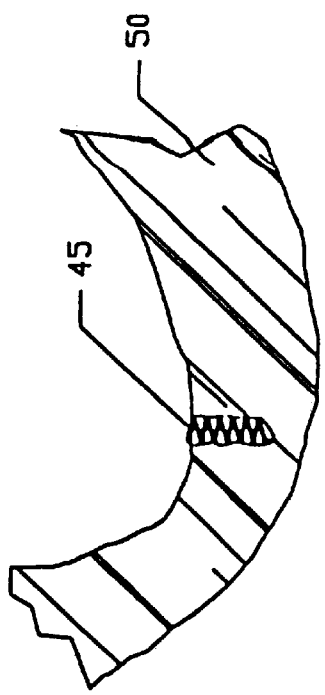
Figure 8H:
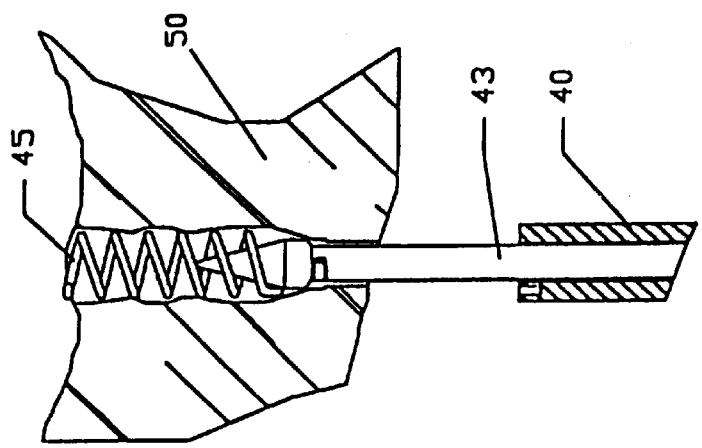
Figure 8G:
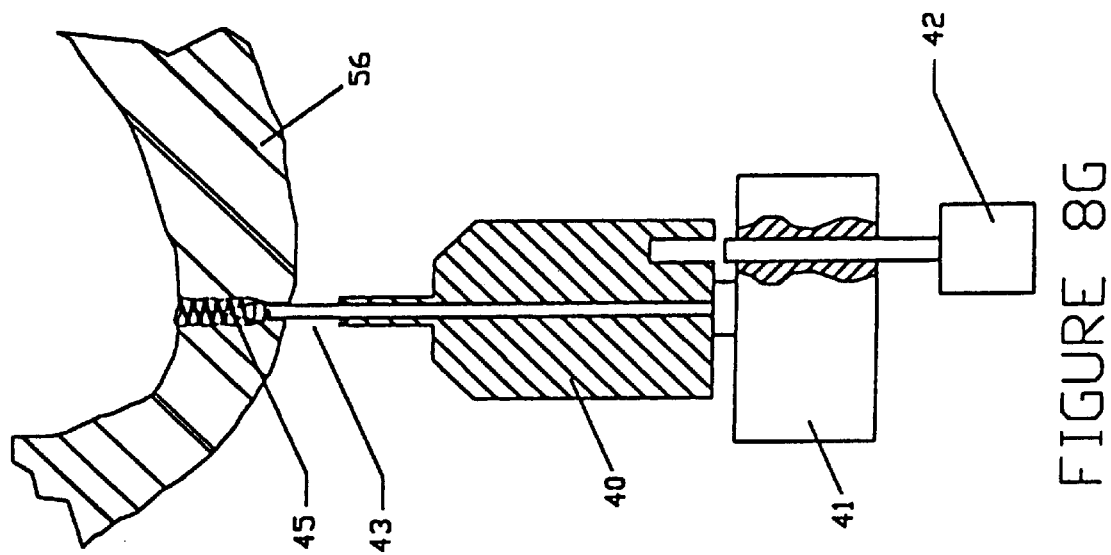

The method of use involves the placement of the implant 45 over an obturator 43. The pin 40 is then rotated to create a radial stress on the TMR implant 45 (FIG. 8D). The pin 40 is locked to the handle 41 (FIG. 8C). Advancement through the heart wall 50 of the obturator and TMR device 45 is achieved by pressing the obturator through the heart wall (FIGS. 8E, 8F). The pin 40 is released from handle 41 by withdrawing the locking device 42 (FIGS. 8G, 8H). This causes the implant 45 to be released from the obturator 43. The obturator 43 is then pulled back from the heart wall 50 leaving the implant 45 imbedded in the heart wall (FIG. 8I).

Figure 9:
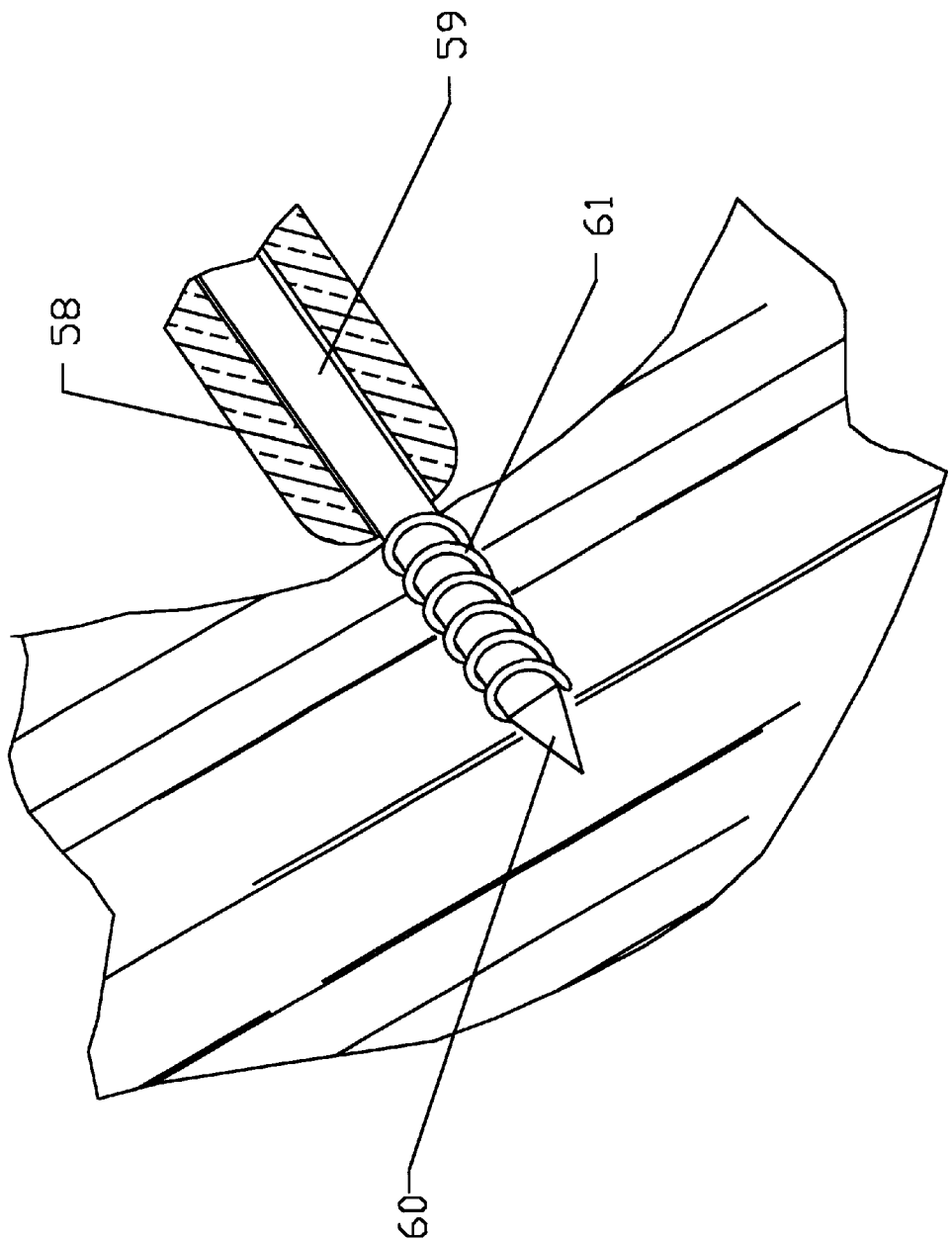
FIG. 9 shows a catheter delivery device and method utilizing a percutaneous access for insertion of a TMR implant into a needle-made space within the heart wall.

FIG. 9 shows a catheter 58 having a slidable wire 59 which terminates at its distal end in a needle point 60. A myocardial implant 61 is mounted proximal to the needle point. Advancing the needle spreads the heart wall tissue and positions the implant 61 into that tissue. Withdrawal of the needle releases the implant 61 in the heart wall.

Figure 10:
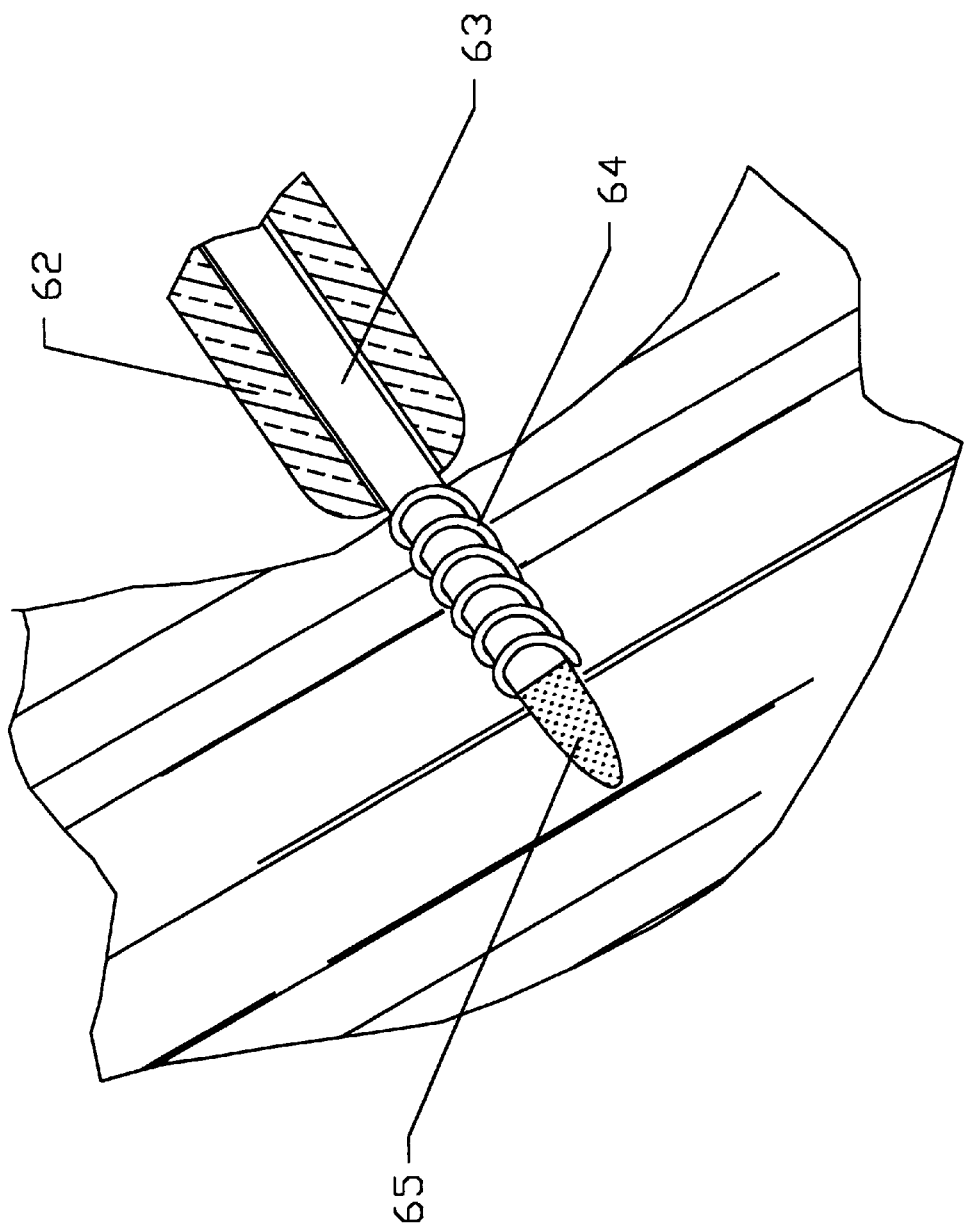
FIG. 10 shows an alternate catheter delivery device and method utilizing a percutaneous access for creating a channel in the heart wall, and for insertion in this channel of a TMR implant.

FIG. 10 shows a catheter 62 which incorporates a slidable wire 63 that terminates at its distal end into a drill or other mechanical attachment 65 for making holes in the heart wall tissue. A myocardial implant 64 is mounted proximal to the drill 65 on the slidable wire 63. Advancing the drilling tool creates a channel in the tissue and positions the implant 64 in this channel. Withdrawal of the drilling tool releases the implant 64 in the heart wall.

FIG. 11 shows a myocardial implant having an anchoring ring retainer or holding means 73 that is coaxial to a main body 70 of a flexible coil. Preferably, the anchoring ring is fabricated as an integral part of the main body of the coil at one end thereof. Preferably, the proximal end of the coil body 70 is formed into a straight wire 72, which is shaped into the anchoring ring 73. Securing elements 71, such as one or more spot welds, join the distal or open end of the coil body 70 to the remainder of that coil. The welds 71 form a joint, which facilitates advancement of the myocardial implant into cardiac tissue, and limits the positioning of the implant on a delivery system.

FIG. 12 is a side view of the myocardial implant of FIG. 11, showing securing elements 74, such as spot welds, that join the open end of the anchoring ring 73. The anchoring ring may have one or more concentric rings with adjacent rings secured together by one or more spot welds 74. The spot welds 74 enhance the integrity of the anchoring ring 73.

Figure 13:
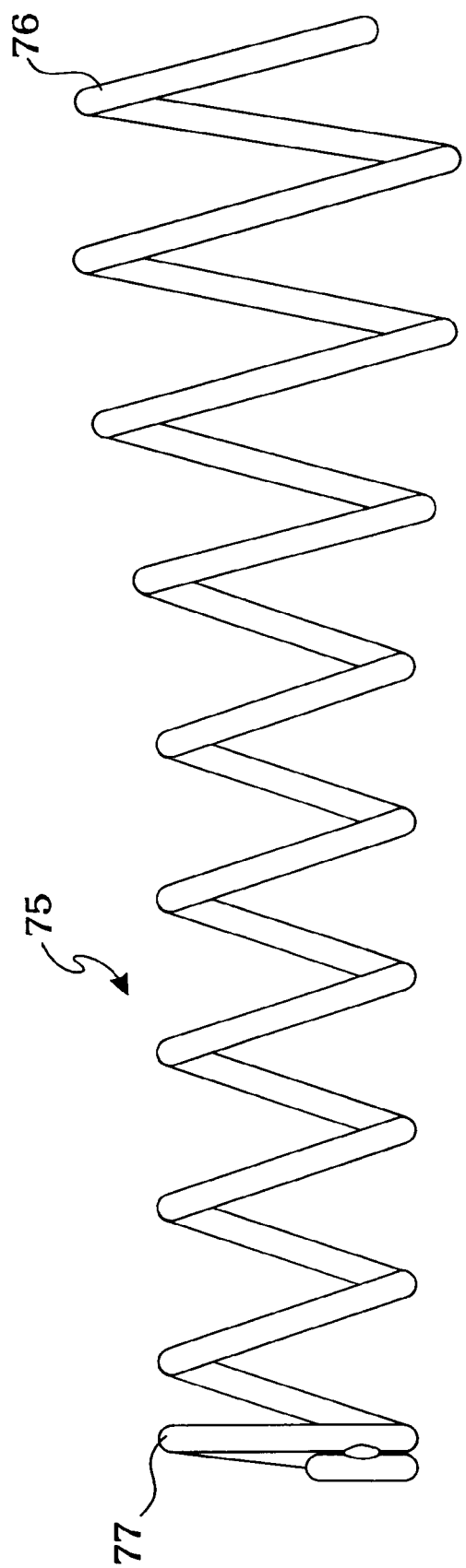
FIG. 13 is a front elevational view of a further embodiment of a TMR impant.

FIG. 13 is a side view of a myocardial implant 75 having a tapered configuration having a first or larger end 76 and a narrower end 77. The larger end 76 provides a self-anchoring means in order to retain the implant 75 in the myocardium. The entire body of the tapered implant 75 is intended to be inserted and held entirely within the myocardium, thus eliminating the need to have an anchoring element, such as a ring protruding outside the heart wall. The second smaller end may include adjacent coils or rings having one or more spot welds holding them together.

The disclosed myocardial implants are expected to incorporate a cavity having a diameter in the range of 1–5 millimeters and a length in the range of 10–30 millimeters. The bodies of the myocardial implants are preferably made of a biocompatible material; such as stainless steel. The myocardial implants may also be coated with a material that promotes angiogenesis (formation of new blood vessels). The myocardial implants may also be made from carbon, gold, platinum, or other suitable materials.

The number of myocardial implants required to be used for each patient depends on the size of the implants and the surface area of the heart segment that is being revascularized. For example, a small segment may require only one myocardial implant, while a large segment may require 10 implants to be implanted in the heart wall.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A myocardial implant for Trans Myocardial Revascularization in a portion of a heart wall, comprising, in combination:
   an elongated, flexible, coil spring body, having an outside surface, an inside surface, an internal cavity and two ends;
   a plurality of openings connecting the internal cavity to the outside surface;
   an anchoring means formed at one of the two ends, coaxial with the elongated, flexible, coil spring body, for holding the elongated, flexible, coil spring body in place in the heart wall opening; and
   the elongated, flexible, coil spring body being a hollow tube, with one of the two ends being completely closed, and the plurality of openings extending between the inside surface and the outside surface.

2. The myocardial implant of claim 1 wherein the elongated coil spring body is coated with a material that resists thrombosis.

3. The myocardial implant of claim 1 wherein the elongated coil spring body includes a material that promotes angiogenesis.

4. The myocardial implant of claim 1 wherein the anchoring means is a ring, and is formed at the completely closed end.

5. A myocardial implant for Trans Myocardial Revascularization in a portion of a heart wall, comprising, in combination:
   an elongated, flexible, coil spring body, having an outside surface, an inside surface, an internal cavity and two ends;
   a plurality of openings connecting the internal cavity to the outside surface;
   an anchoring means formed at one of the two ends, coaxial with the elongated, flexible, coil spring body, for holding the elongated, flexible, coil spring body in place in the heart wall opening; and
   the elongated, flexible, coil spring body has adjacent end coils at a second of the two ends; and the adjacent end coils are held together by means for securing the adjacent end coils.

6. The myocardial implant of claim 5 wherein the means for securing the adjacent end coils is at least one spot weld.

7. The myocardial implant of claim 6 wherein the elongated, flexible, coil spring body is tapered and has a first, larger end, and a second, smaller end; and the anchoring means is the first, larger end.

8. A myocardial implant for Trans Myocardial Revascularization in a portion of a heart wall, comprising, in combination:
   an elongated, flexible, coil spring body, having an outside surface, an inside surface, an internal cavity and two ends;
   a plurality of openings connecting the internal cavity to the outside surface;
   an anchoring means formed at one of the two ends, coaxial with the elongated, flexible, coil spring body, for holding the elongated, flexible, coil spring body in place in the heart wall opening;
   the elongated, flexible, coil spring body is tapered having a first larger end and a second smaller end; and the anchoring means is the first larger end.

9. A myocardial implant for Trans Myocardial Revascularization in a portion of a heart wall, comprising, in combination:
   an elongated, flexible, coil spring body, having an outside surface, an inside surface, an internal cavity and two ends;
   a plurality of openings connecting the internal cavity to the outside surface;
   an anchoring means formed at one of the two ends, coaxial with the elongated, flexible, coil spring body, for holding the elongated, flexible, coil spring body in place in the heart wall opening; and
   the anchoring means has a plurality of rings, and the plurality of rings are held together by means for securing the plurality of rings.

10. The myocardial implant of claim 9 wherein the means for securing the plurality of rings is at least one spot weld.

11. The myocardial implant of claim 10 wherein there are a plurality of spot welds securing the plurality of rings together.

12. The myocardial implant of claim 11 wherein a second of the two ends includes adjacent end coils and the adjacent end coils are held together by means for securing the adjacent end coils.

13. The myocardial implant of claim 12 wherein the means for securing the adjacent end coils is at least one spot weld.

14. A myocardial implant for Trans Myocardial Revascularization comprising, in combination:

a flexible, elongated coil spring body having an outside surface, an inside surface, an internal cavity and two ends;

a plurality of openings connecting the inside surface to the outside surface;

a coaxial anchoring means formed at a first of the ends for securing the myocardial implant in a myocardium wall; and the coaxial anchoring means having a plurality of concentric rings held together by at least one spot weld.

15. The myocardial implant of claim 14, further including abutting end coils at a second of the two ends; the abutting end coils being held together by at least one spot weld.

16. A myocardial implant for Trans Myocardial Revascularization comprising, in combination:

a flexible, elongated coil spring body having an outside surface, an inside surface, an internal cavity and two ends;

a plurality of openings connecting the inside surface to the outside surface;

a coaxial anchoring means formed at a first of the ends for securing the myocardial implant in a myocardium wall;

the elongated, flexible, coil spring body is tapered and has a first, larger end and a second, smaller end; and the first, larger end is the anchoring means.

17. A myocardial implant for Trans Myocardial Revascularization comprising, in combination:

a flexible, elongated coil spring body having an outside surface, an inside surface, an internal cavity and two ends;

a plurality of openings connecting the inside surface to the outside surface;

a coaxial anchoring means formed at a first of the ends for securing the myocardial implant in a myocardium wall; and the coaxial anchoring means has a plurality of concentric rings held together by a plurality of spot welds.

18. A myocardial implant for insertion into a heart wall comprising, in combination:

a flexible, tubular body in the form of a coil spring having an outside surface, an inside surface and two ends;

one of the two ends being completely closed;

an internal cavity bound by the inside surface and the completely closed end;

a plurality of openings formed in the flexible, tubular body connecting the internal cavity to the outside surface; and the myocardial implant being adapted to be entirely secured within the heart wall.

19. The myocardial implant of claim 18, further including an anchor formed at the completely closed end.

* * * * *